(12) United States Patent
Oharu et al.

(10) Patent No.: US 7,425,646 B2
(45) Date of Patent: *Sep. 16, 2008

(54) FLUORINATED ADAMANTANE DERIVATIVE

(75) Inventors: Kazuya Oharu, Yokohama (JP);
Takashi Okazoe, Yokohama (JP);
Eisuke Murotani, Yokohama (JP);
Kunio Watanabe, Yokohama (JP);
Masahiro Ito, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/611,183

(22) Filed: Dec. 15, 2006

(65) Prior Publication Data

US 2007/0083064 A1    Apr. 12, 2007

Related U.S. Application Data

(63) Continuation of application No. PCT/JP2005/010374, filed on Jun. 6, 2005.

(30) Foreign Application Priority Data

Jun. 16, 2004   (JP) .............................. 2004-178330

(51) Int. Cl.
  *C07C 69/63* (2006.01)
(52) U.S. Cl. ...................... 560/227; 560/226; 562/582; 562/849; 562/850; 562/852
(58) Field of Classification Search ................. 560/227, 560/226; 562/582, 849, 850, 852
See application file for complete search history.

(56) References Cited

U.S. PATENT DOCUMENTS

| 4,284,558 | A  | 8/1981  | Barton et al. |
| 7,084,295 | B2 | 8/2006  | Tanaka et al. |
| 7,326,512 | B2 | 2/2008  | Ogata et al.  |
| 2005/0277785 | A1 | 12/2005 | Okazoe et al. |
| 2005/0288528 | A1 | 12/2005 | Okazoe et al. |

FOREIGN PATENT DOCUMENTS

| JP | 57-79187 | 5/1982 |
| JP | A-57-79187 | * 5/1982 |
| JP | 9-43848 | 2/1997 |
| WO | WO 00/56694 | 9/2000 |
| WO | WO 03/055841 A1 | 7/2003 |
| WO | WO 2004/050725 A1 | 6/2004 |
| WO | WO 2004/052832 A1 | 6/2004 |

OTHER PUBLICATIONS

H.Duddeck, M.Spitzer, G.Bolte□□Syntheses and 13C-NMR spectroscopic investigation of trifluoromethyl-substituted adamantanes□□Liebigs Ann.Chem. 1985, 545-554.*
H. Duddeck, et al., "Synthesen UND 13C-NMR-Spektroskopische Untersuchungen Trifluormethylsubstituierter Adamantane", Liebigs Ann. Chem., 1985, No. 3, pp. 545-554.
Farcasiu et al, J. Am. Chem. Soc., 1985, vol. 107, pp. 5717-5722.
Adcock et al, J. Org. Chem., 1996, vol. 61, pp. 5073-5076.
Manoharan et al, Tetrahedron Letters, 1995, vol. 36, No. 21, pp. 3651-3654.
Adcock et al, J. Org. Chem., 1992, vol. 57, pp. 4749-4752.
U.S. Appl. No. 11/611,183, filed Dec. 15, 2006, Oharu et al.
U.S. Appl. No. 11/567,391, filed Dec. 6, 2006, Shu Wang et al.
Farcasiu et al, J. Am. Chem. Soc., 1985, vol. 107, pp. 5717-5722.
Adcock et al, J. Org. Chem., 1996, vol. 61, pp. 5073-5076.
Manoharan et al, Tetrahedron Letters, 1995, vol. 36, No. 21, pp. 3651-3654.
Adcock et al, J. Org. Chem., 1992, vol. 57, pp. 4749-4752.

* cited by examiner

*Primary Examiner*—Yvonne Eyler
*Assistant Examiner*—Sudhakar Katakam
(74) *Attorney, Agent, or Firm*—Oblon, Spivak, McClelland, Maier & Neustadt, P.C.

(57) ABSTRACT

A compound represented by the formula $A^F(\text{—COF})_n$, provided that $A^F$ and n have the following meanings.

$A^F$: a fluorinated adamantane residue which is an n-valent group having an n number of hydrogen atoms removed from adamantane (provided that when n is at least 2, the removed hydrogen atoms are hydrogen atoms bonded to different carbon atoms), wherein at least one of the remaining hydrogen atoms is substituted by a fluorine atom, and the remaining hydrogen atoms may be substituted by a $C_{1-6}$ alkyl group or fluoroalkyl group, and
  n: an integer of from 1 to 4,
  provided the when n is 1, $A^F$ has at least one hydrogen atom.

9 Claims, No Drawings

FLUORINATED ADAMANTANE DERIVATIVE

BACKGROUND OF THE INVENTION

1. Field of the Invention

The present invention relates to novel fluorinated adamantane derivatives.

2. Discussion of Background

Fluoroadamantane compounds having such a structure that fluorine atoms are bonded to carbon atoms constituting the adamantane ring (hereinafter referred to as a fluoroadamantane skeleton), have both a rigid structure derived from the adamantane skeleton and properties derived from fluorine atoms and are thereby excellent in various physical properties. Accordingly, various such compounds and processes for producing such compounds have been studied. For example, as a process for producing a perfluoro(alkyl group-substituted adamantane), a process for producing a compound represented by the following formula (b) which comprises subjecting a compound represented by the following formula (a) to electrolytic fluorination in anhydrous hydrofluoric acid in the presence of an inert gas (JP-A-57-079187).

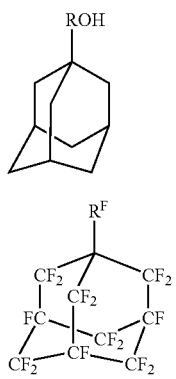

(a)

(b)

wherein R in ROH is a $C_{1-4}$ linear alkylene group, and OH is located at the terminal of R, and $R^F$ is a $C_{1-4}$ perfluorinated linear alkyl group.

However, with respect to a compound having such a structure that a —COF group is bonded to the fluoroadamantane skeleton, only perfluoroadamantanecarboxylic acid fluoride obtained by electrolytic fluorination of 1-adamantanemethanol has been reported in JP-A-57-079187. Further, with respect to the physical properties of the acid fluoride, only the reactivity with methanol to form methyl (perfluoroadamantane)carboxylate has been disclosed in JP-A-57-079187.

That is, compounds having a —COF group at a specific portion of the fluoroadamantane skeleton, particularly compounds having at least two —COF groups in the fluoroadamantane skeleton, and physical properties and usefulness of these compounds, have not been known yet.

SUMMARY OF THE INVENTION

Under these circumstances, the present inventors have conducted extensive studies and as a result, found fluoroadamantane compounds (preferably perfluoroadamantane compounds) having at least one (preferably 2, 3 or 4) —COF group on the carbon atom constituting the adamantane ring. They have further found that these compounds, which have a reactive —COF group, are useful as materials of various derivatives.

Namely, the present invention provides the following.

(1) A compound represented by the following formula (5)

$$A^F(-COF)_n \qquad (5)$$

provided that the symbols in the formula have the following meanings:

$A^F$: a fluorinated adamantane residue which is an n-valent group having an n number of hydrogen atoms removed from adamantane (provided that when n is at least 2, the removed hydrogen atoms are hydrogen atoms bonded to different carbon atoms), wherein at least one of the remaining hydrogen atoms is substituted by a fluorine atom, and the remaining hydrogen atoms may be substituted by a $C_{1-6}$ alkyl group or fluoroalkyl group, and n: an integer of from 1 to 4, provided the when n is 1, $A^F$ has at least one hydrogen atom.

(2) The compound according to (1), wherein $A^F$ is a group having an n number of hydrogen atoms bonded to a tertiary carbon atom of adamantane removed from adamantane.

(3) The compound according to (1) or (2), wherein n is 2, 3 or 4.

(4) A compound represented by the following formula (5a):

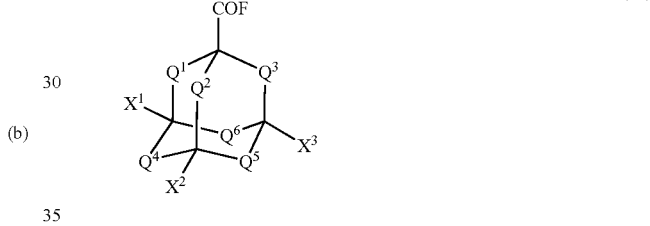

(5a)

provided that the symbols in the formula have the following meanings:

each of $X^1$, $X^2$ and $X^3$ which are independent of one another, is a hydrogen atom, a fluorine atom or a —COF group; and each of $Q^1$, $Q^2$, $Q^3$, $Q^4$, $Q^5$ and $Q^6$ which are independent of one another, is a —$CF_2$— group or a —CHF— group, provided that when all of $X^1$, $X^2$ and $X^3$ are fluorine atoms, at least one of $Q^1$, $Q^2$, $Q^3$, $Q^4$, $Q^5$ and $Q^6$ is a —CHF— group.

(5) The compound according to (4), wherein $Q^1$, $Q^2$, $Q^4$, $Q^5$ and $Q^6$ are —$CF_2$— groups and $Q^3$ is a —CHF— group.

(6) A compound represented by the following formula (5b):

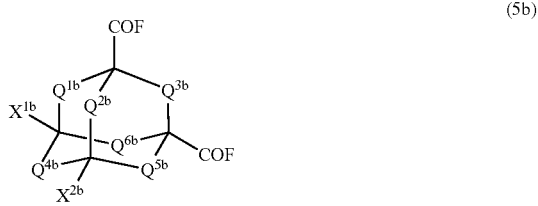

(5b)

provided that the symbols in the formula have the following meanings:

each of $X^{1b}$ and $X^{2b}$ which are independent of each other, is a fluorine atom or a hydrogen atom; and each of $Q^{1b}$, $Q^{2b}$, $Q^{3b}$, $Q^{4b}$, $Q^{5b}$ and $Q^{6b}$ which are independent of one another, is a —$CF_2$— group or a —CHF— group, provided that at least four of them are —$CF_2$— groups.

(7) A compound represented by the following formula (5c):

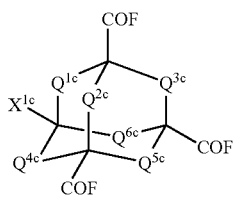

(5c)

provided that the symbols in the formula have the following meanings:

$X^{1c}$ is a fluorine atom or a hydrogen atom; and each of $Q^{1c}$, $Q^{2c}$, $Q^{3c}$, $Q^{4c}$, $Q^{5c}$ and $Q^{6c}$ which are independent of one another, is a —$CF_2$— group or a —CHF— group, provided that at least four of them are —$CF_2$— groups.

(8) A compound represented by the following formula (5d):

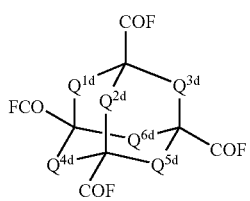

(5d)

provided that the symbols in the formula have the following meanings:

each of $Q^{1d}$, $Q^{2d}$, $Q^{3d}$, $Q^{4d}$, $Q^{5d}$ and $Q^{6d}$ which are independent of one another, is a —$CF_2$— group or a —CHF— group, provided that at least four of them are —$CF_2$— groups.

(9) A compound selected from compounds represented by the following formulae:

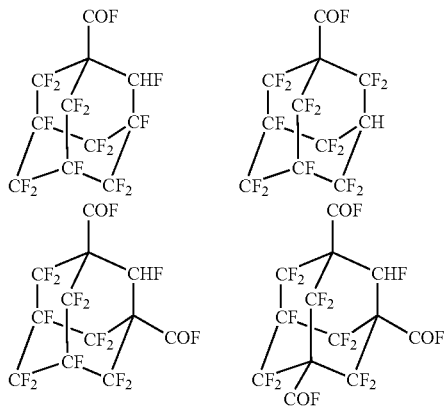

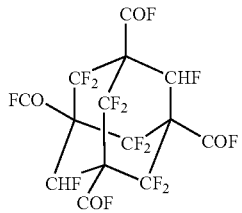

The compounds of the present invention are compounds having a fluoroadamantane residue, and are thereby excellent in physical properties such as heat resistance, light resistance, chemical resistance, low refractive index properties, water repellency, oil repellency and transparency. Further, the compounds of the present invention, which have at least one reactive —COF group, can be converted into various derivatives having the above physical properties by chemical conversion of the —COF group.

DETAILED DESCRIPTION OF THE PREFERRED EMBODIMENTS

In this specification, a compound represented by the formula (1) will be referred to as a compound (1). The same applies to compounds represented by other formulae.

Adamantane is a $C_{10}H_{16}$ saturated polycyclic hydrocarbon represented by the following formula. In this specification, an adamantane ring represents this carbon ring constituted by ten carbon atoms. The adamantane ring is constituted by four tertiary carbon atoms and six secondary carbon atoms, as represented by the following formula.

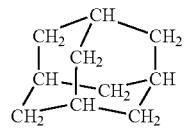

The present invention provides the following compound (5):

$$A^F(-COF)_n \qquad (5)$$

In the above formula, $A^F$ is an n-valent group having an n number of hydrogen atoms removed from adamantane (provided that when n is at least 2, the removed hydrogen atoms are hydrogen atoms bonded to different carbon atoms), and is a group having at least one of the remaining hydrogen atoms substituted by a fluorine atom. Further, this n-valent group may have hydrogen atoms, and at least some of the remaining hydrogen atoms may be substituted by a $C_{1-6}$ alkyl group or fluoroalkyl group, but they are preferably not substituted. n is an integer of from 1 to 4, provided that when n is 1, the above $A^F$ has at least one hydrogen atom.

Accordingly, to the carbon atoms in the adamantane ring of the above $A^F$ (fluorinated adamantane residue), fluorine atoms are bonded. Further, the carbon atoms in the adamantane ring of $A^F$ are such that at least one of them has a bond to which a —COF group, in addition to fluorine atoms, is bonded, at least one hydrogen atom is optionally (essentially in a case where n is 1) is bonded to the carbon atom, and optionally at least one alkyl group or fluoroalkyl group is bonded (both may be bonded) to the carbon atom. Here, a highly fluorinated adamantane residue means a fluorinated adamantane residue having substantially no hydrogen atoms bonded to carbon atoms in the adamantane ring.

In $A^F$, the hydrogen atom removed from adamantane may be a hydrogen atom bonded to a secondary carbon atom or may be a hydrogen atom bonded to a tertiary carbon atom among carbon atoms in the adamantane ring, and is particularly preferably a hydrogen atom bonded to a tertiary carbon atom. However, in a case where 2 to 4 hydrogen atoms are removed, all the hydrogen atoms must be hydrogen atoms bonded to different carbon atoms. In a case where n is 2 to 4, as well as a case where n is 1, all hydrogen atoms removed are preferably hydrogen atoms bonded to tertiary carbon atoms. Namely, all the —COF groups are preferably bonded to tertiary carbon atoms. n is preferably 2, 3 or 4.

In a case where $A^F$ has a hydrogen atom, the hydrogen atom may be bonded to a tertiary carbon atom in the adamantane ring, or may be bonded to a secondary carbon atom, and in a case where $A^F$ has at least two hydrogen atoms, they may be bonded to both types of the carbon atoms. The hydrogen atom bonded to a carbon atom in the adamantane ring is preferably a hydrogen atom bonded to a secondary carbon atom, and in such a case, the secondary carbon atom preferably has one hydrogen atom bonded thereto. That is, the secondary carbon atom having a hydrogen atom is preferably a —CHF— group. The tertiary carbon atom preferably has no hydrogen atom bonded thereto.

The number of hydrogen atoms bonded to carbon atoms in the adamantane ring is preferably at most half the total number of fluorine atoms and hydrogen atoms bonded to carbon atoms in the adamantane ring. The number of hydrogen atoms bonded to carbon atoms in the adamantane ring is more preferably at most 6 in total, furthermore preferably at most 3. That is, in a case where $A^F$ has a hydrogen atom, the number of hydrogen atoms bonded to carbon atoms in the adamantane ring is preferably from 1 to 3.

In a case where n is 1, presence of a hydrogen atom bonded to a carbon atom in the adamantane ring is essential, and the number of such a hydrogen atom is preferably at most 3, particularly preferably 1. The hydrogen atom is preferably a hydrogen atom bonded to a secondary carbon atom (provided that one secondary carbon atom has only one hydrogen atom) as mentioned above.

In a case where $A^F$ has a $C_{1-6}$ alkyl group or a $C_{1-6}$ fluoroalkyl group, such a group may be bonded to a tertiary carbon atom in the adamantane ring or may be bonded to a secondary carbon atom, and in a case where $A^F$ has at least two such groups, they may be bonded to both types of the carbon atoms. In a case where an alkyl group or a fluoroalkyl group is bonded to a carbon atom in the adamantane ring, the number of such groups is preferably at most 3 in total, more preferably 1. More preferred $A^F$ has no such groups.

The above alkyl group or fluoroalkyl group preferably has from 1 to 4 carbon atoms, particularly preferably one carbon atom. Further, a fluoroalkyl group is preferred to an alkyl group, a perfluoroalkyl group is more preferred, and a trifluoromethyl group is particularly preferred.

$A^F$ is preferably a fluorinated adamantane residue having no alkyl group nor fluoroalkyl group and having at most 3 hydrogen atoms. More preferred $A^F$ is a fluorinated adamantane residue having no alkyl group nor fluoroalkyl group, having n of from 2 to 4 and having no hydrogen atom (i.e. a bivalent to tetravalent perfluoroadamantane). In addition, the bonds to which —COF are bonded in such a preferred fluorinated adamantane residue are all bonds on tertiary carbon atoms.

The compound (5) of the present invention is produced preferably by subjecting the following compound (4X) or the following compound (4Y) to decomposition reaction (provided that $A^F$ and n are as defined above). The decomposition reaction is carried out preferably in the presence of a catalyst. The catalyst is preferably NaF or KF.

(4X),

(4Y).

Here, $R^F$ is a polyfluoroalkyl group which may contain an etheric oxygen atom.

The polyfluoroalkyl group is preferably a $C_{1-20}$ perfluoroalkyl group or a $C_{1-20}$ perfluoroalkyl group containing an etheric oxygen atom.

The perfluoroalkyl group may, for example, be $CF_3CF_2$—, $CF_3CF_2CF(CF_3)$— or $(CF_3)_2CF$—.

The perfluoroalkyl group containing an etheric oxygen atom may, for example, be $F(CF_2)_3OCF(CF_3)$— or $F(CF_2)_3OCF(CF_3)CF_2OCF(CF_3)$—.

The compound (4X) is prepared preferably by a process of subjecting the following compound (1X) and the following compound (2X) to esterification reaction to obtain the following compound (3X), and then subjecting the compound (3X) to liquid phase fluorination reaction to obtain the following compound (4X).

 (1X)

 (2X)

 (3X)

 (4X)

Here, $A^F$ and n are as defined above. Z is a halogen atom, preferably a fluorine atom or a chlorine atom. A has the following meaning.

A: An adamantane residue which is an n-valent group having an n number of hydrogen atoms removed from adamantane (provided that when n is at least 2, the removed hydrogen atoms are hydrogen atoms bonded to different carbon atoms), wherein the remaining hydrogen atoms may be substituted by a $C_{1-6}$ alkyl group.

The compound (4Y) is prepared preferably by a process of subjecting the following compound (1Y) and the following compound (2Y) to esterification reaction to obtain the following compound (3Y), and then subjecting the compound (3Y) to liquid phase fluorination reaction to obtain the following compound (4Y).

 (1Y)

 (2Y)

 (3Y)

 (4Y)

Here, $A^F$, A, $R^F$, n and Z are as defined above.

In these processes, the esterification reaction and the liquid phase fluorination reaction are carried out preferably in accordance with methods disclosed in WO00/56694, WO02/4397, WO02/26689, etc. by the present applicant.

In the esterification reaction of the compound (1X) and the compound (2X), the amount of the compound (2X) to the compound (1X) is preferably at least n mols, particularly preferably from (1 to 2)n times by mol, especially preferably from (1 to 1.1)n times by mol (provided that n is as defined above). Further, in the esterification reaction of the compound (1Y) and the compound (2Y), the amount of the compound (2Y) to the compound (1Y) is preferably at most n mols, particularly preferably (0.5 to 1)n times by mol, especially preferably (0.9 to 1.1)n times by mol (provided that n is as defined above).

In a case where these compounds (4X) and (4Y) are obtained by the above processes, $A^F$ in the compound (4X) and $A^F$ in the compound (4Y) form a highly fluorinated adamantane residue, but a fluorinated adamantane residue having a hydrogen atom not fluorinated may be formed in some cases. In such a case, each of the compounds (4X) and (4Y) is present as a composition, which may be used as a material for the above decomposition reaction without isolation and purification.

The compound (5) of the present invention is preferably the following compound (5a) (provided that $Q^1$, $Q^2$, $Q^3$, $Q^4$, $Q^5$, $Q^6$, $X^1$, $X^2$ and $X^3$ are as defined above):

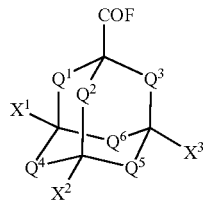
(5a)

At least four of $Q^1$, $Q^2$, $Q^3$, $Q^4$, $Q^5$ and $Q^6$ are preferably —$CF_2$— groups, and each of them is particularly preferably —$CF_2$— group. Further, at least one of $X^1$, $X^2$ and $X^3$ is preferably a —COF group.

The compound (5a) of the present invention is preferably the following compound (5b), (5c) or (5d):

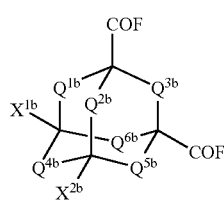
(5b)

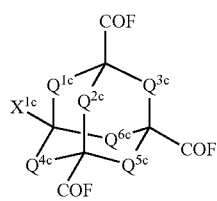
(5c)

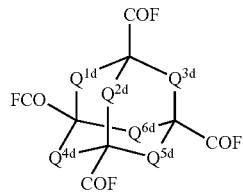
(5d)

wherein $X^{1b}$, $X^{2b}$, $Q^{1b}$, $Q^{2b}$, $Q^{3b}$, $Q^{4b}$, $Q^{5b}$, $Q^{6b}$, $X^{1c}$, $Q^{1c}$, $Q^{2c}$, $Q^{3c}$, $Q^{4c}$, $Q^{5c}$, $Q^{6c}$, $Q^{1d}$, $Q^{2d}$, $Q^{3d}$, $Q^{4d}$, $Q^{5d}$ and $Q^{6d}$ are as defined above.

In the compound (5b), each of $X^{1b}$ and $X^{2b}$ is preferably a fluorine atom. $Q^{1b}$, $Q^{2b}$, $Q^{3b}$, $Q^{4b}$, $Q^{5b}$ and $Q^{6b}$ are preferably such that they are —$CF_2$— group, or at least four of them are —$CF_2$— group and at least one is a —CHF— group, particularly preferably such that they are —$CF_2$— groups, or $Q^{1b}$, $Q^{2b}$, $Q^{4b}$, $Q^{5b}$ and $Q^{6b}$ are —$CF_2$— groups and $Q^{3b}$ is a —CHF— group.

In the compound (5c), $X^{1c}$ is preferably a fluorine atom. $Q^{1c}$, $Q^{2c}$, $Q^3$, $Q^{4c}$, $Q^{5c}$ and $Q^{6c}$ are preferably such that they are —$CF_2$— groups, or at least four of them are —$CF_2$— groups and at least one is a —CHF— group, particularly preferably such that they are —$CF_2$— groups, or $Q^{1c}$, $Q^{2c}$, $Q^{4c}$, $Q^{5c}$ and $Q^{6c}$ are —$CF_2$— groups and $Q^{3c}$ is a —CHF— group.

In the compound (5d), $Q^{1d}$, $Q^{2d}$, $Q^{3d}$, $Q^{4d}$, $Q^{5d}$ and $Q^{6d}$ are preferably such that they are —$CF_2$— groups, or at least four of them are —$CF_2$— groups and at least one is a —CHF— group, particularly preferably such that they are —$CF_2$— groups, or $Q^{1d}$, $Q^{2d}$, $Q^{5d}$ and $Q^{6d}$ are —$CF_2$— groups and $Q^{3d}$ and $Q^{4d}$ are —CHF— groups.

As specific examples of the compound (5b), the following compounds may be mentioned.

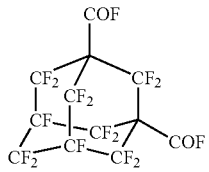 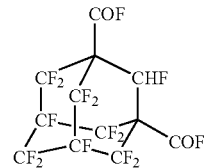

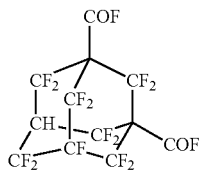 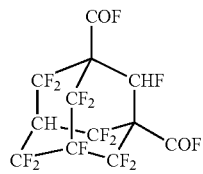

As specific examples of the compound (5c), the following compounds may be mentioned.

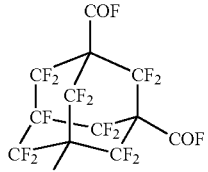 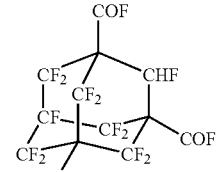

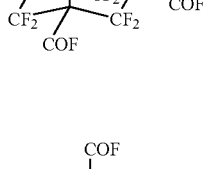 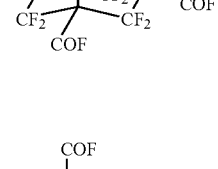

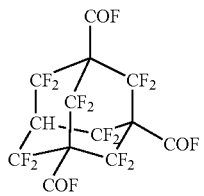 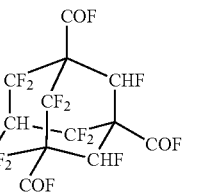

As specific examples of the compound (5d), the following compounds may be mentioned.

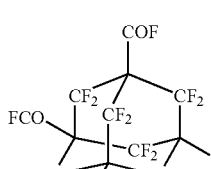 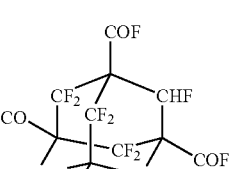

As specific examples of the compound (5a) other than the compounds (5b), (5c) and (5d), the following compounds may be mentioned.

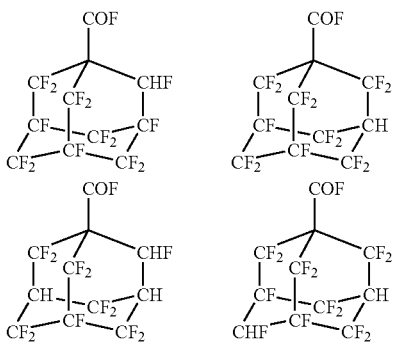

The compounds of the present invention are compounds characterized by having such a structure that n —COF group is bonded to highly fluorinated adamantane (wherein n is as defined above). Among the compounds of the present invention, compounds wherein n is 2, 3 or 4 are useful as e.g. a crosslinking agent or a polymerizable monomer, or a material of a crosslinking agent or a polymerizable monomer. As a method for producing a polymer employing such a compound as a polymerizable monomer, for example, a method of reacting the following compound (5b21) with ethylene glycol to produce a polymer containing the following units (5B211) may be mentioned.

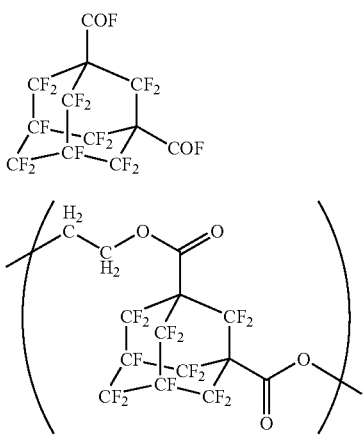

Such a polymer can be excellent in heat resistance, mold release properties, chemical resistance, and transparency and light resistance against short wavelength light because of the units, and is thereby useful as various functional materials.

Now, the present invention will be described in further detail with reference to Examples. However, it should be understood that the present invention is by no means restricted to such specific Examples.

In Examples, 1,1,2-trichloro-1,2,2-trifluoroethane will be referred to as R-113, dichloropentafluoropropane as R-225, and tetramethylsilane as TMS. As R-225, a mixed product of $CF_3CF_2CHCl_2$ and $CF_2ClCF_2CHFCl$ was used. The pressure is shown by a gauge pressure. Gas chromatography will be referred to as GC. Gas chromatography mass spectrometry will be referred to as GC-MS. The yield was determined by $^{19}F$-NMR measurement employing hexafluorobenzene as an internal standard. The selectivity was determined by the peak area ratio in GC analysis.

EXAMPLE 1

Example (1) for Preparation of Compounds (5a11), (5a12) and (5a13)

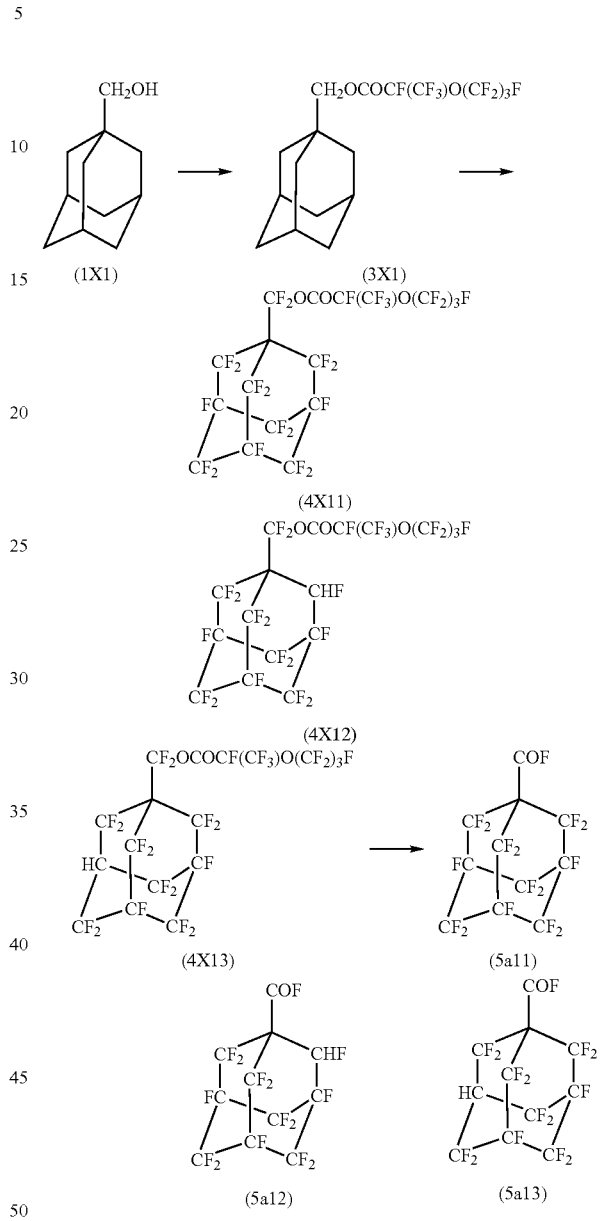

EXAMPLE 1-1

Example for preparation of compound (3X1)

Compound (1X1) (8 g) and chloroform (40 mL) were put into a flask and stirred while bubbling nitrogen gas. FCOCF$(CF_3)O(CF_2)_3F$ (25.5 g) was dropwise added over a period of 1 hour while the internal temperature of the is flask was maintained at 30° C. After completion of the dropwise addition, the mixture was stirred at 30° C. for 3 hours while the internal temperature was maintained at 30° C. Then, while the internal temperature of the flask was maintained at 15° C. or lower, a saturated sodium hydrogencarbonate aqueous solution (50 mL) was added to obtain a liquid which was separated into two layers of an organic layer and an aqueous layer.

The organic layer in the liquid was recovered and washed twice with water (50 mL) and dried over anhydrous magnesium sulfate, followed by filtration to obtain a crude liquid. The crude liquid was purified by silica gel column chromatography (developing solvent: R-225) to obtain the above compound (3X1) (20.4 g).

NMR spectrum data of the compound (3X1) are shown below.

$^1$H-NMR (300.4 MHz, solvent: CDCl$_3$, standard: TMS) δ (ppm): 1.50 to 1.80(m,12H), 2.01(bs,3H), 3.87(d,J=10.7 Hz,1H), 4.04(d,J=10.7 Hz,1H).

$^{19}$F-NMR (282.7 MHz, solvent: CDCl$_3$, standard: CFCl$_3$) δ (ppm): −80.2(1F), −81.3(3F), −82.0(3F), −86.4(m,1F), −129.5 (2F), −131.3(1F).

EXAMPLE 1-2

Example for Preparation of Compounds (4X11), (4X12) and (4X13)

Into an autoclave (internal capacity: 500 mL, made of nickel), R-113 (312 g) was introduced, stirred and maintained at 25° C. At a gas outlet of the autoclave, a condenser maintained at 20° C., a NaF pellet packed layer and a condenser maintained at 10° C. were installed in series. Further, from the condenser maintained at −10° C., a liquid-returning line was installed to return the condensed liquid to the autoclave. After blowing nitrogen gas for 1.0 hour, fluorine gas diluted to 20% with nitrogen gas (hereinafter referred to as 20% fluorine gas) was blown at a flow rate of 9.97 L/h for 1 hour. Then, while the 20% fluorine gas was blown at the same flow rate, a solution having the compound (3X1) (5.0 g) obtained in Example 1-1 dissolved in R-113 (102 g) was injected over a period of 4.7 hours.

Then, while the 20% fluorine gas was blown at the same flow rate and the pressure of the autoclave was maintained at 0.15 MPa, a R-113 solution having a benzene concentration of 0.01 g/mL (hereinafter referred to as a benzene solution) was injected in an amount of 9 mL while the internal temperature of the autoclave was raised from 25° C. to 40° C., whereupon the benzene inlet of the autoclave was closed, and stirring was continued for 0.3 hour.

Then, while the pressure in the autoclave was maintained at 0.15 MPa and the temperature in the autoclave was maintained at 40° C., the benzene solution (6 mL) was injected, and stirring was further continued for 0.3 hour. Then, while the pressure in the autoclave was maintained at 0.15 MPa and the temperature in the autoclave was maintained at 40° C., the benzene solution (8.5 mL) was injected, and stirring was further continued for 1.0 hour. The total amount of benzene injected was 0.24 g, and the total amount of R-113 injected was 23.5 mL. Further, nitrogen gas was blown for 1.0 hour, and the content in the autoclave was recovered.

The content was analyzed by GC-MS analysis and $^{19}$F-NMR and confirmed to be a mixture of the above compound (4X11) (yield: 29%) and a compound (yield: 71%) having one fluorine atom bonded to a carbon atom in adamantane of the compound (4X11) substituted by a hydrogen atom. Further, as a result of analysis by $^1$H-NMR, formation of the above compounds (4X12) and (4X13) was confirmed.

$^{19}$F-NMR spectrum data of the compound (4X11) are shown below.

$^{19}$F-NMR (376.0 MHz, solvent: CDCl$_3$, standard: CFCl$_3$) δ (ppm): −61.9(2F), −79.0 to −81.0(1F), −82.0(3F), −82.1 (3F), −85.5 to −88.0(1F), −109.0 to −116.0(6F), −117.0 to −125.0(6F), −130.1(2F), −131.6 to −133.5 (1F), −217.0 to −222.0(3F).

$^1$H-NMR spectrum data of the compound (4X12) are shown below.

$^1$H-NMR (399.8 MHz, solvent: CDCl$_3$, standard: TMS) δ (ppm): 5.71(d,J$_{FH}$=46.0 Hz, 1H).

$^1$H-NMR spectrum data of the compound (4X13) are shown below.

$^1$H-NMR (399.8 MHz, solvent: CDCl$_3$, standard: TMS) δ (ppm): 3.79(m,1H).

EXAMPLE 1-3

Example for Preparation of Compounds (5a11), (5a12) and (5a13)

The mixture (5.3 g) obtained in Example 1-2 was charged together with KF powder (0.3 g) into a flask. The flask was immersed in an oil bath at from 80 to 90° C. and heated for 4 hours with vigorous stirring. At the top of the flask, a reflux condenser adjusted at a temperature of 20° C. and a pack made of a fluororesin film (Tedler Pack, tradename, manufactured by Du Pont) were installed in series. Then, the flask was cooled to recover a liquid sample (3.4 g) The liquid sample was analyzed by GC-MS analysis and $^{19}$F-NMR and confirmed to be a mixture of the above compound (5a11), a compound having one fluorine atom bonded to a carbon atom in adamantane of the compound (5a11) substituted by a hydrogen atom and CF$_3$CF(OCF$_2$CF$_2$CF$_3$)COF. Further, as a result of $^1$H-NMR analysis, formation of the above compounds (5a12) and (5a13) was confirmed.

$^{19}$F-NMR spectrum data of the compound (5a11) are shown below.

$^{19}$F-NMR (376.0 MHz, solvent: CDCl$_3$, standard: CFCl$_3$) δ (ppm): 55.9(1F), −110.0 (6F), −120.5(6F), −218.9(3F).

$^1$H-NMR spectrum data of the compound (5a12) are shown below.

$^1$H-NMR (399.8 MHz, solvent: CDCl$_3$, standard: TMS) δ (ppm): 5.70(d,J$_{FH}$=45.9 Hz,1H).

$^1$H-NMR spectrum data of the compound (5a13) are shown below.

$^1$H-NMR (399.8 MHz, solvent: CDCl$_3$, standard: TMS) δ (ppm): 3.92(m,1H).

EXAMPLE 2

Example (2) for Preparation of Compounds (5a11), (5a12) and (5a13).

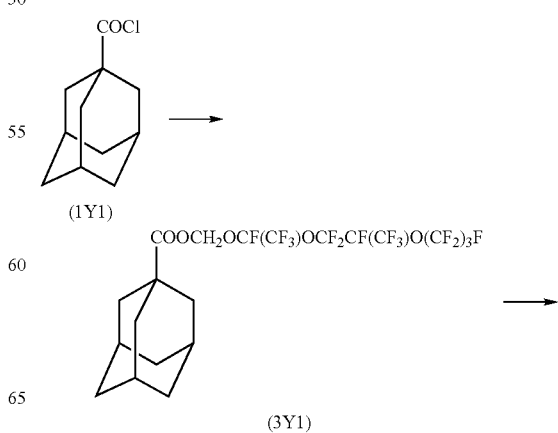

-continued

COOCF₂OCF(CF₃)OCF₂CF(CF₃)O(CF₂)₃F

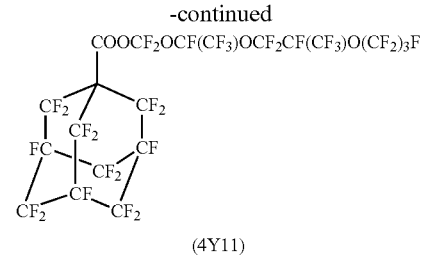

(4Y11)

COOCF₂OCF(CF₃)OCF₂CF(CF₃)O(CF₂)₃F

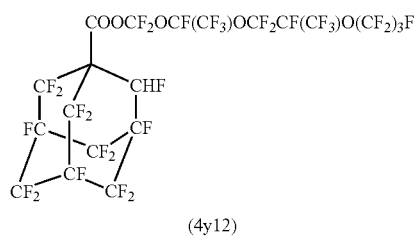

(4y12)

COOCF₂OCF(CF₃)OCF₂CF(CF₃)O(CF₂)₃F

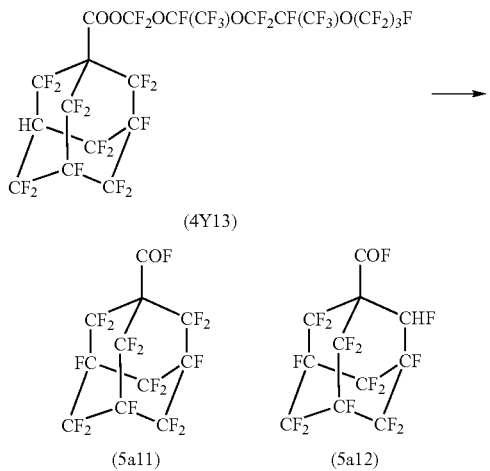

(4Y13)

(5a11)    (5a12)

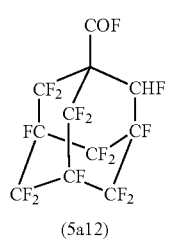

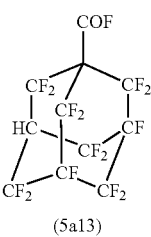

(5a13)

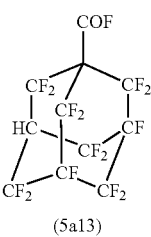

EXAMPLE 2-1

Example for Preparation of Compound (3Y1)

Compound (1Y1) (1.95 g, 9.8 mmol) and pyridine (1.00 g, 12.6 mmol) were put into a round-bottomed flask (internal capacity: 50 ml), and F(CF₂)₃OCF(CF₃)CF₂OCF(CF₃)CH₂OH (4.61 g, 9.6 mmol) was dropwise added with stirring while the internal temperature of the flask was maintained at 25° C. After completion of the dropwise addition, the internal temperature of the flask was raised to 50° C. with stirring, and then stirring was carried out for 5 hours while the internal temperature was maintained at from 45 to 50° C.

Then, R-225 was added to the flask, and the obtained diluted liquid was washed with a diluted hydrochloric acid aqueous solution and water in this order, anhydrous magnesium sulfate was added thereto, and the liquid was left at rest for 12 hours. Magnesium sulfate was removed by filtration, and the filtrate was concentrated by an evaporator to obtain a concentrated product (5.47 g). The concentrated product was analyzed by GC and NMR analyses and as a result, formation of the above compound (3Y1) was confirmed (selectivity: 83.8%, yield: 74.4%).

NMR spectrum data of the compound (3Y1) are shown below.

$^1$H-NMR (300.4 MHz, solvent: CDCl₃, standard: TMS) δ (ppm): 1.73(m,6H), 1.90(s,6H), 2.03(s,3H), 4.58(m,2H).

$^{19}$F-NMR (282.7 MHz, solvent: CDCl₃, standard: CFCl₃) δ (ppm): −79.8 to −80.6(4F), −81.8 to −83.4(9F), −130.1(2F), −133.9(1F), −145.5(1F).

EXAMPLE 2-2

Example for Preparation of Compounds (4Y11), (4Y12) and (4Y13)

The same autoclave as in Example 1-2 was prepared, and the 20% fluorine gas was blown at a flow rate of 11.31 L/h for 30 minutes while the internal temperature of the autoclave was maintained at 25° C. Further, the pressure in the autoclave was raised to 0.20 MPa, whereupon the 20% fluorine gas was blown at the same flow rate for 30 minutes.

Then, while the pressure in the autoclave was maintained at 0.20 MPa and the 20% fluorine gas was blown at the same flow rate, a solution having the compound (4 g) obtained in Example 2-1 dissolved in R-113 (80 g) was injected over a period of 3.3 hours.

Then, a reaction was carried out in the same manner as in Example 1-2 except that the pressure in the autoclave was maintained at 0.20 MPa, that injection of the benzene solution was repeated five times, that the total amount of benzene injected was 0.45 g, and that the total amount of R-113 injected was 45 mL. After the reaction, the internal pressure of the reactor was adjusted to atmospheric pressure, and nitrogen gas was blown for 1 hour.

The content in the autoclave was analyzed by GC-MS analysis and $^{19}$F-NMR and confirmed to be a mixture of the above compound (4Y11) (yield: 86%) and a compound (yield: 11%) having one fluorine atom bonded to a carbon atom in adamantane of the compound (4Y11) substituted by a hydrogen atom. Further, as a result of $^1$H-NMR, formation of the above compounds (4Y12) and (4Y13) was confirmed.

$^{19}$F-NMR spectrum data of the compound (4Y11) are shown below.

$^{19}$F-NMR (376.0 MHz, solvent: CDCl₃, standard: CFCl₃) δ (ppm): −61.9(2F), −79.0 to −81.0(1F), −82.0(3F), −82.1 (3F), −85.5 to −88.0(1F), −109.0 to −116.0(6F), −117.0 to −125.0(6F), −130.1(2F), −131.6 to −133.5(1F), −217.0 to −222.0(3F).

$^1$H-NMR spectrum data of the compound (4Y12) are shown below. $^1$H-NMR (399.8 MHz, solvent: CDCl₃, standard: TMS) δ (ppm): 5.71(d,J$_{FH}$=46.0 Hz,1H).

$^1$H-NMR data of the compound (4Y13) are shown below.

$^1$H-NMR (399.8 MHz, solvent: CDCl₃, standard: TMS) δ (ppm): 3.79(m,1H).

EXAMPLE 2-3

Example for Preparation of Compounds (5a11), (5a12) and (5a13)

The mixture (4.8 g, 5.0 mmol) obtained in Example 2-2 and KF powder (0.09 g, 1.5 mmol) were charged into a round-bottomed flask (internal capacity: 50 mL). The flask was immersed in an oil bath at 140° C. and heated for 1 hour with vigorous stirring. At the top of the flask, a reflux condenser adjusted at a temperature of 20° C. and a liquid receiver were installed.

A liquid sample (3.2 g) distilled on the liquid receiver was analyzed by GC-MS analysis, $^{19}$F-NMR and $^{1}$H-NMR and confirmed to be a mixture of compounds (5a11) and (5a12) and $F(CF_2)_3OCF(CF_3)CF_2OCF(CF_3)COF$.

EXAMPLE 3

Example for Preparation of Compounds (5b21) and (5b22).

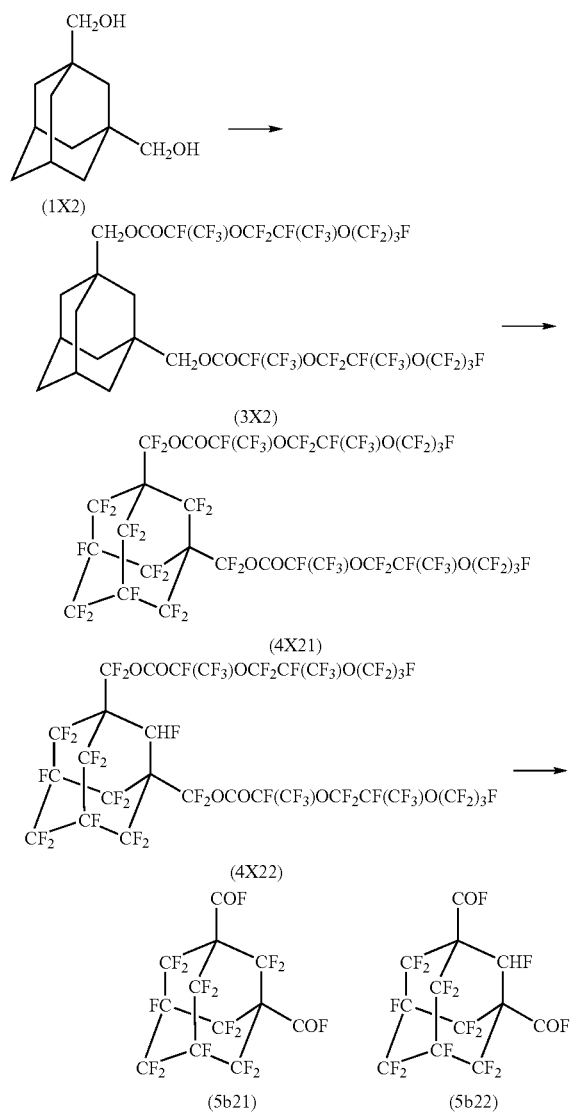

EXAMPLE 3-1

Example for Preparation of Compounds (3X2)

Compound (1X2) (0.78 g) and NaF (0.83 g) were put in a round-bottomed flask (internal capacity: 50 mL), and R-225 was added thereto, followed by stirring in a suspension state. $F(CF_2)_3OCF(CF_3)CF_2OCF(CF_3)COF$ (5.74 g) was dropwise added with stirring while the temperature in the flask was maintained at 25° C. After completion of the dropwise addition, the temperature in the flask was raised to 65 to 70° C. with stirring, and stirring was continued for 3 hours.

Then, R-225 was added to the flask and the obtained solution in the flask was subjected to filtration to remove NaF, thereby to obtain a crude reaction liquid. The crude reaction liquid was washed with a saturated sodium hydrogencarbonate aqueous solution and a saturated salt solution three times. It was further washed twice with deionized water, then magnesium sulfate was added, and the liquid was left at rest for 1 hour. Then, the liquid was subjected to filtration to remove magnesium sulfate, and the obtained filtrate was concentrated by an evaporator and further vacuum concentrated by a vacuum pump to obtain a concentrated product (2.46 g). The concentrated product was analyzed by GC and NMR and as a result, formation of the above compound (3X2) was confirmed (selectivity: 99.7%, yield: 46%).

NMR spectrum data of the compound (3X2) are shown below.

$^{1}$H-NMR (300.4 MHz, solvent: CDCl$_3$, standard: TMS): 1.39(s,2H), 1.53(m,8H), 1.68(s,2H), 2.16(s,2H), 3.88 to 4.12 (m,4H).

$^{19}$F-NMR (282.7 MHz, solvent: CDCl$_3$, standard: CFCl$_3$): −80.0 to −81.0(8F), −81.9 to −82.8(16F), −84.5 to −85.4(2F), −130.2(4F), −131.9(2F), −145.6(2F).

EXAMPLE 3-2

Example for Preparation of Compounds (4X21) and (4X22)

The same autoclave as in Example 1-2 was prepared, and nitrogen gas was blown for 1.0 hour while the internal temperature of the autoclave was maintained at 25° C. The 20% fluorine gas was blown at a flow rate of 9.05 L/h for 30 minutes, and the autoclave internal pressure was raised to 0.15 MPa, whereupon the 20% fluorine gas was blown further for 30 minutes. Then, while the 20% fluorine gas was blown at the same flow rate, a solution having the compound (3X2) (2.46 g) obtained in Example 2-1 dissolved in R-113 (49.03 g) was injected over a period of 1.3 hours.

A reaction was carried out under the same conditions as in Example 1-2 (provided that the total amount of benzene injected was 0.34 g, and the total amount of R-113 injected was 33 mL). After the reaction, the pressure in the autoclave was adjusted to atmospheric pressure, and nitrogen gas was blown for 1 hour.

The content in the autoclave was analyzed by GC-MS analysis and $^{19}$F-NMR and confirmed to be a mixture of the above compound (4X21) (yield: 76%) and a compound (yield: 18%) having one fluorine atom bonded to a carbon atom in adamantane of the compound (4X21) substituted by a hydrogen atom. Further, as a result of $^{1}$H-NMR analysis, formation of the above compound (4X22) was confirmed.

$^{19}$F-NMR spectrum data of the compound (4X21) are shown below.

$^{19}$F-NMR (282.7 MHz, solvent: CDCl$_3$, standard: CFCl$_3$): −79.5 to −80.6(8F), −82.0 to −82.3(20F), −84.4 to −85.0(2F), −98.4 to −121.5(12F), −130.2(4F), −132.1(2F), −145.5(2F), −217.9(2F).

$^1$H-NMR spectrum data of the compound (4X22) are shown below.

$^1$H-NMR(399.8 MHz, solvent: CDCl$_3$, standard: TMS) δ (ppm): 5.80(d,J$_{FH}$=44.2 Hz,1H).

EXAMPLE 3-3

Example for Preparation of Compounds (5b21) and (5b22)

The mixture (2.39 g) obtained in Example 3-2 was charged together with KF powder (0.08 g) into a flask. At the top of the flask, a reflux condenser adjusted at a temperature of 20° C. and a pack made of a fluororesin film (Tedler Pack, tradename, manufactured by Du Pont) were installed in series. The flask was immersed in an oil bath at from 117 to 120° C. and heated for 3 hours with vigorous stirring. Then, the flask was cooled, and the KF powder was removed by filtration through a filter to recover a liquid sample (2.00 g).

The liquid sample was analyzed by GC, GC-MS analysis and $^{19}$F-NMR and confirmed to be a mixture of the above compound (5b21), a compound having at least one fluorine atom bonded to adamantane of the compound (5b21) substituted by a hydrogen atom and CF$_3$(CF$_2$)$_2$OCF(CF$_3$)CF$_2$OCF (CF$_3$)COF. Further, as a result of $^1$H-NMR analysis, formation of the above compound (5b22) was confirmed.

$^{19}$F-NMR spectrum data of the compound (5b21) are shown below.

$^{19}$F-NMR (283.7 MHz, solvent: CDCl$_3$, standard: CFCl$_3$) δ (ppm): 55.4(2F), −97.9(2F), −109.9(8F), −120.8(2F), −217.8(2F).

$^1$H-NMR and $^{19}$F-NMR spectrum data of the compound (5b22) are shown below.

$^1$H-NMR (300.4 MHz, solvent: CDCl$_3$, standard: TMS) δ (ppm): 5.95(d,J$_{FH}$=42.3 Hz, 1H).

$^{19}$F-NMR (282.7 MHz, solvent: CDCl$_3$, standard: CFCl$_3$) δ (ppm): 49.4(2F), −107.4 to −112.0(8F), −120.8(2F), −204.7 (1F), −217.8 to −218.4(2F).

EXAMPLE 4

Example for Preparation of Compound (5d41)

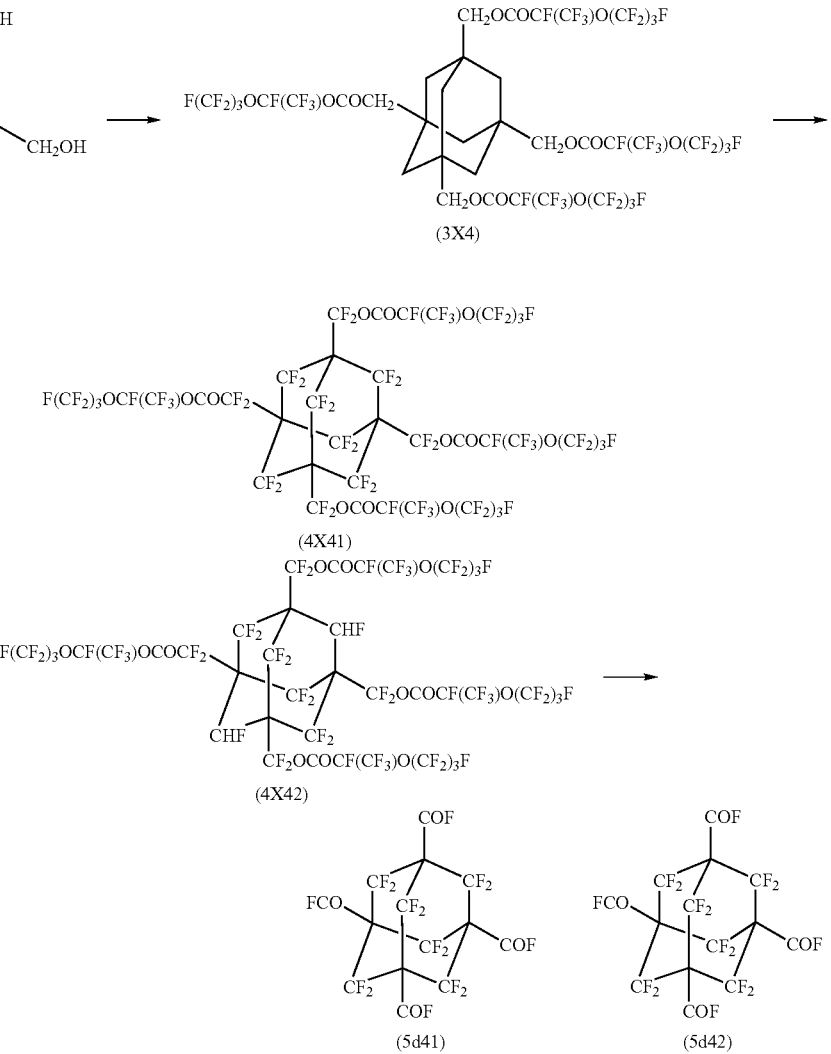

EXAMPLE 4-1

Example for Preparation of Compound (3X4)

The above compound (3X4) is obtained by carrying out a reaction in the same manner as in Example 3-1 except that the above compound (1X4) is used instead of the compound (1X2) and $CF_3(CF_2)_2OCF(CF_3)COF$ is used instead of $CF_3(CF_2)_2OCF(CF_3)CF_2OCF(CF_3)COF$.

EXAMPLE 4-2

Example for Preparation of Compounds (4X41) and (4X22)

A product containing as the main component a fluorinated product of the compound (3X4) is obtained by carrying out a reaction in the same manner as in Example 3-2 by using the compound (3X4) in Example 4-1. The product is analyzed by GC-MS analysis and $^{19}$F-NMR and as a result, formation of a mixture of the above compound (4X41) and a compound having at least one fluorine atom bonded to a carbon atom in adamantane of the compound (4X41) substituted by a hydrogen atom is confirmed. Further, as a result of $^1$H-NMR analysis, formation of the above compound (4X42) is confirmed.

EXAMPLE 4-3

Example for Preparation of Compounds (5d41) and (5d42)

A reaction is carried out in the same manner as in Example 3-3 by using the mixture in Example 4-2. The product is analyzed by GC-MS analysis and $^{19}$F-NMR and as a result, formation of a mixture of the above compound (5d41) and a compound having at least one fluorine atom bonded to a carbon atom in adamantane of the compound (5d41) substituted by a hydrogen atom is confirmed. Further, as a result of $^1$H-NMR analysis, formation of the above compound (4d42) is confirmed.

EXAMPLE 5

Example for Preparation of Compound (1X3)

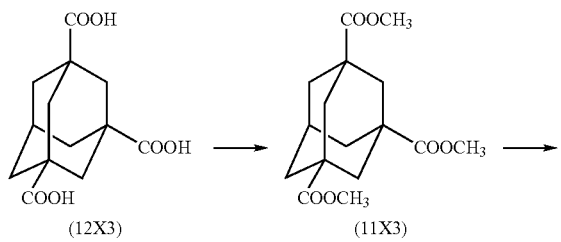

EXAMPLE 5-1

Example for Preparation of Compound (11X3)

Compound (12X3) (30.27 g) and methanol (93.38 g) were charged into a round-bottomed flask (internal capacity: 300 mL), and concentrated sulfuric acid (15.12 g) was added thereto under cooling in a water bath, followed by stirring in a suspension state. Then, the solution in the flask was stirred in a state where it is circulated by heating for 2 hours, whereupon the solution in the flask became transparent.

The solution in the flask was cooled and concentrated, water (200 mL) and toluene were added thereto, and components extracted into toluene were recovered to obtain a white solid product (33.38 g). As a result of GC and NMR analyses of the product, formation of compound (12X3) was confirmed.

NMR spectrum data of the compound (12X3) are shown below.

$^1$H-NMR (300.4 MHz, solvent: $CDCl_3$, standard: TMS) δ (ppm): 3.68(s,9H), 2.30(m,1H), 1.84 to 2.07(m,12H).

EXAMPLE 5-2

Example for Preparation of Compound (1X3)

A toluene solution (120 g) containing 65 mass % of sodium bis(2-methoxyethoxy)aluminum hydride and toluene (150 mL) were charged into a round-bottomed flask (internal capacity: 500 mL), and the solution in the flask was cooled in a water bath with stirring. Then, a solution having compound (11X3) (33.38 g) dissolved in toluene (100 mL) was dropwise added to the flask. The solution in the flask was stirred further for 1 hour in a state where it was circulated by heating.

The solution in the flask was cooled and concentrated, water (60 mL) was added thereto, and an aqueous solution (120 g) containing 15 mass % of sodium hydroxide was further added thereto to obtain a reaction liquid. The reaction liquid was continuously extracted with chloroform, and the obtained white solid product (22.27 g) was analyzed by GC and NMR and as a result, formation of substantially pure compound (1X3) was confirmed.

NMR spectrum data of the compound (1X3) are shown below.

$^1$H-NMR (300.4 MHz, solvent: $CDCl_3$, standard: TMS) δ (ppm): 4.32(t,3H), 3.04(d,6H), 2.05(s,1H), 1.30(s,6H), 1.10 (q,6H).

EXAMPLE 6

Example for Preparation of Compound (5c31) and Example for Preparation of Compound (5c32)

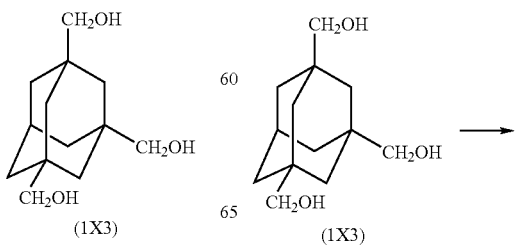

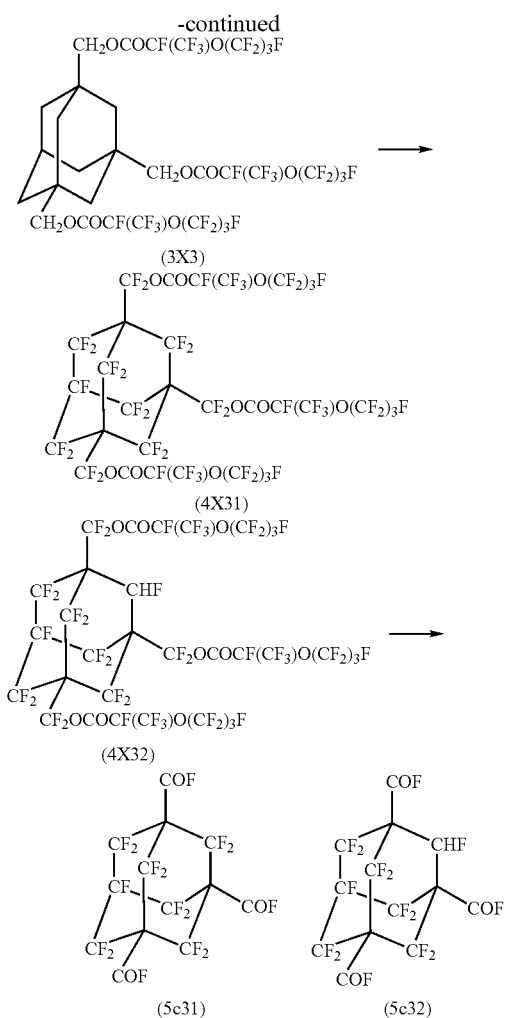

EXAMPLE 6-1

Example for Preparation of Compound (3X3)

Into a reactor (internal capacity: 1.0 L, made of PFA), compound (1X3) (22.27 g), NaF (55.26 g) and R-225 (490 g) were put and stirred in a suspension state. F(CF$_2$)$_3$OCF(CF$_3$)COF (118.53 g) was dropwise added with stirring while the internal temperature of the flask was maintained at 25° C. After completion of the dropwise addition, stirring was continued for 10 hours.

Then, the solution in the flask was subjected to filtration to remove NaF, and the filtrate was concentrated by an evaporator and further vacuum concentrated by a vacuum pump to obtain a concentrated product (114.39 g). As a result of GC and NMR analyses of the concentrated product, formation of the above compound (3X3) was confirmed. The concentrated product was purified by column chromatography (developing solvent: R-225) to obtain pure compound (3X3) (106.22 g) (yield: 93%).

NMR and IR spectrum data of the compound (3X3) are shown below.

$^1$H-NMR (300.4 MHz, solvent: CDCl$_3$, standard: TMS) δ (ppm): 4.13 (d,3H), 3.95(d,3H), 2.32(s,1H), 1.52(s,6H), 1.38 (s,6H).

$^{19}$F-NMR (282.7 MHz, solvent: CDCl$_3$, standard: CFCl$_3$) δ (ppm): −80.0 to −81.0(3F), −81.9(9F), −82.6(9F), −86.6 to −87.2(3F), −130.3(6F), −132.2(3F).

IR(neat): 747, 992, 1037, 1117, 1151, 1234, 1287, 1333, 1463, 1786, 2861, 2919 cm$^{-1}$.

EXAMPLE 6-2

Example for Preparation of Compounds (4X31) and (4X32)

An autoclave (internal capacity: 3L, made of nickel) was prepared, and at a gas outlet of the autoclave, a condenser maintained at 20° C., a NaF pellet packed layer and a condenser maintained at −10° C. were installed in series. Further, from the condenser maintained at −10° C., a liquid-returning line was installed to return the condensed liquid to the autoclave.

R-113 (1,600 g) was charged to the autoclave, followed by stirring while the temperature was maintained at 25° C. Continuously, nitrogen gas was blown to the autoclave at 25° C. for 1 hour, and then fluorine gas diluted to 20 vol % with nitrogen gas (hereinafter referred to as 20% fluorine gas) was blown at 25° C. at a flow rate of 16.05 L/h for 1 hour. Then, while the 20% fluorine gas was blown at the same flow rate, a solution having the compound (3X3) obtained in Example 6-1 dissolved in R-113 (700 g) was injected over a period of 20.0 hours.

Then, while the 20% fluorine gas was blown at the same flow rate, the internal pressure of the autoclave was raised to 0.15 MPa (gauge pressure), and a R-113 solution having a benzene concentration of 6 mg/mL was injected in an amount of 110 mL while the temperature was raised from 25° C. to 40° C., whereupon the benzene solution inlet of the autoclave was closed.

Further, while the 20% fluorine gas was blown at the same flow rate, stirring was continued for 1 hour. Then, the pressure in the reactor was adjusted to atmospheric pressure, and nitrogen gas was blown for 1 hour. The content in the autoclave was analyzed by NMR and confirmed to be a mixture of the above compounds (4X31) and (4X32).

$^{19}$F-NMR spectrum data of the compound (4X31) are shown below.

$^{19}$F-NMR (282.6 MHz, solvent: CDCl$_3$, standard: C$_6$F$_6$) δ (ppm): −80.1 to −82.3(27F), −85.9 to −86.6(3F), −96.0 to −112.8(12F), −130.2(6F), −132.1(3F), −218.5 to −220.0(1F).

$^1$H-NMR and $^{19}$F-NMR spectrum data of the compound (4X32) are shown below.

$^1$H-NMR (399.8 MHz, solvent: CDCl$_3$, standard: TMS) δ (ppm): 5.83 (d,J$_{FH}$=44.2 Hz,1H).

$^{19}$F-NMR (282.6 MHz, solvent: CDCl$_3$, standard: C$_6$F$_6$) δ (ppm): −80.1 to −82.3(27F), −85.9 to −86.6(3F), −96.0 to −112.8(10F), −130.2(6F), −132.1(3F), −210.6 to −211.5(1F) −218.5 to −220.0(1F).

EXAMPLE 6-3

Example for Preparation of Compounds (5c31) and (5c32)

The same reaction as in Example 3-3 is carried out by using the mixture obtained in Example 6-2. The product is analyzed by GC-MS analysis and $^{19}$F-NMR and confirmed to be a mixture of the above compound (5c31) and a compound having at least one fluorine atom bonded to a carbon atom in adamantane of the compound (5c32) substituted by a hydrogen atom. As a result of $^1$H-NMR analysis, the above compound (5c32) is confirmed to be the main component.

The compounds of the present invention, which have a reactive —COF group, are useful as polymerizable monomers and materials of various derivatives. Further, the derivatives are excellent in transparency and light resistance (particularly against short wavelength light), heat resistance, etc. and are thereby useful as materials of functional materials, crosslinking agents, intermediates for pharmaceutical and agricultural chemicals, etc.

The entire disclosure of Japanese Patent Application No. 2004-178330 filed on Jun. 16, 2004 including specification, claims and summary is incorporated herein by reference in its entirety.

What is claimed is:

1. A compound represented by the following formula (5)

provided that the symbols in the formula have the following meanings:

$A^F$: a fluorinated adamantane residue which is an n-valent group having an n number of hydrogen atoms removed from adamantane (provided that when n is at least 2, the removed hydrogen atoms are hydrogen atoms bonded to different carbon atoms), wherein at least one of the remaining hydrogen atoms is substituted by a fluorine atom, and the remaining hydrogen atoms may be substituted by a $C_{1-6}$ alkyl group or fluoroalkyl group, and n: an integer of from 2 to 4.

2. The compound according to claim 1, wherein $A^F$ is a group having an n number of hydrogen atoms bonded to a tertiary carbon atom of adamantane removed from adamantane.

3. A compound represented by the following formula (5b):

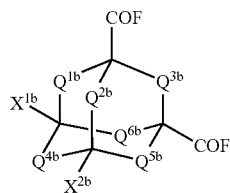

provided that the symbols in the formula have the following meanings:

each of $X^{1b}$ and $X^{2b}$ which are independent of each other, is a fluorine atom or a hydrogen atom; and each of $Q^{1b}$, $Q^{2b}$, $Q^{3b}$, $Q^{4b}$, $Q^{5b}$ and $Q^{6b}$ which are independent of one another, is a —$CF_2$— group or a —CHF— group, provided that at least four of them are —$CF_2$— groups.

4. A compound represented by the following formula (5c):

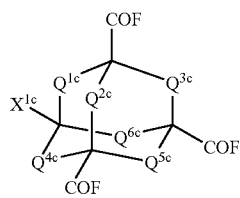

provided that the symbols in the formula have the following meanings:

$X^{1c}$ is a fluorine atom or a hydrogen atom; and each of $Q^{1c}$, $Q^{2c}$, $Q^{3c}$, $Q^{4c}$, $Q^{5c}$ and $Q^{6c}$ which are independent of one another, is a —$CF_2$— group or a —CHF— group, provided that at least four of them are —$CF_2$— groups.

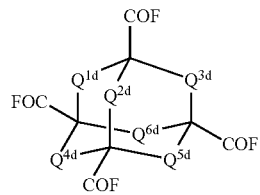

provided that the symbols in the formula have the following meanings:

each of $Q^{1d}$, $Q^{2d}$, $Q^{3d}$, $Q^{4d}$, $Q^{5d}$ and $Q^{6d}$ which are independent of one another, is a —$CF_2$— group or a —CHF— group, provided that at least four of them are —$CF_2$— groups.

6. A compound selected from compounds represented by the following formulae:

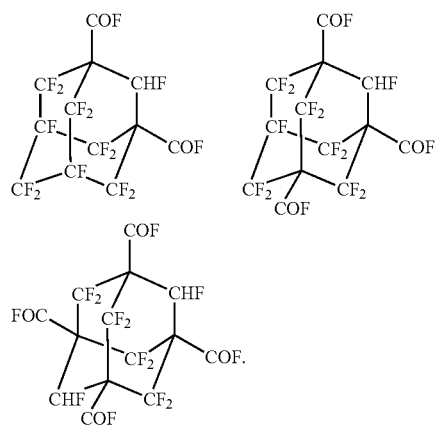

7. The compound according to claim 6, wherein the compound is of the following formula:

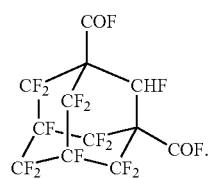

8. The compound according to claim 6, wherein the compound is of the following formula:

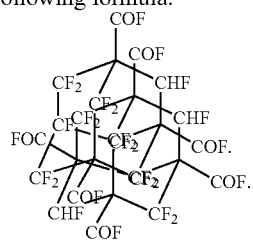

9. The compound according to claim 6, wherein the compound is of the following formula:

* * * * *